United States Patent [19]

Katzer et al.

[11] Patent Number: 5,215,718
[45] Date of Patent: Jun. 1, 1993

[54] LABORATORY DRYER WITH HYDROPHILIC EXHAUST FILTER

[76] Inventors: Rodney A. Katzer, 12 Elm St., R.D. #4, Chester, N.J. 07930; Charles F. McBrairty, 2801 Northampton St., Easton, Pa. 18042; Edward J. McBrairty, 80 Vista Dr., Warminster, Pa. 18974

[21] Appl. No.: 893,103

[22] Filed: Jun. 3, 1992

Related U.S. Application Data

[63] Continuation of Ser. No. 503,218, Apr. 2, 1990, abandoned.

[51] Int. Cl.⁵ .................. B01L 9/00; F26B 21/06
[52] U.S. Cl. .................. 422/102; 422/124; 34/80; 34/82
[58] Field of Search ............ 422/104, 124; 34/80–82, 219; 55/5.27, DIG. 42, DIG. 43, DIG. 45

[56] References Cited

U.S. PATENT DOCUMENTS

| | | | |
|---|---|---|---|
| 2,623,301 | 12/1952 | Weiskopf | 34/82 |
| 2,933,154 | 4/1960 | Lauterbach | 34/82 X |
| 3,031,381 | 4/1962 | Langerhans | 34/80 X |
| 3,482,703 | 12/1969 | Roberts et al. | 210/489 |
| 3,703,961 | 11/1972 | Feuer | 210/151 |
| 3,724,177 | 4/1973 | Grote | 55/515 X |
| 3,910,778 | 10/1975 | Shahgholi | 55/102 |
| 4,020,230 | 4/1977 | Mahoney et al. | 55/527 X |
| 4,224,743 | 9/1980 | Erickson et al. | 34/219 |
| 4,276,819 | 7/1981 | Goldman et al. | 422/104 X |
| 4,344,775 | 8/1982 | Klien | 55/527 X |
| 4,482,703 | 11/1984 | Takahashi et al. | 528/322 |
| 4,602,110 | 8/1986 | Frazier | 55/74 |
| 4,670,223 | 6/1987 | Delachapelle | 422/122 |
| 4,773,990 | 9/1988 | Hood, Jr. | 55/498 X |
| 4,922,626 | 5/1990 | Fiddler | 34/80 |

Primary Examiner—James C. Housel
Assistant Examiner—Arlen Soderquist
Attorney, Agent, or Firm—Eckert Seamans Cherin & Mellott

[57] ABSTRACT

A laboratory dryer especially for drying potentially infectious or toxic samples has a housing with an air inlet and an air outlet, the housing defining an air flow path. The samples are received at a station between the inlet and the outlet along the air flow path, and subjected to a powered air flow via a fan. A hydrophilic filter element intersects the air flow downstream along the air flow path from the samples and upstream of the outlet, and captures particulate matter and water droplets which would otherwise be carried by the air flow from the housing into the room where the dryer is located. An electric heater is disposed in the housing adjacent the inlet and downstream of the fan. The housing can have an internal cross section of decreasing area proceeding towards the samples along the air flow path, whereby a velocity of the air over the samples is increased. The housing defines a plurality of compartments for receiving the samples along sections separated by internal partitions of the housing disposed parallel to the flowpath. The hydrophilic filter element is a fibrous batt of fibers disposed across the outlet, preferably synthetic fibers such as polyethylene fibers, mounted in a frame whereby the filter element can be readily removed.

15 Claims, 2 Drawing Sheets

LABORATORY DRYER WITH HYDROPHILIC EXHAUST FILTER

CROSS REFERENCE TO RELATED APPLICATION

This is a continuation of application Ser. No. 503,218, filed Apr. 2, 1990, abandoned concurrently with filing of this application.

BACKGROUND OF THE INVENTION

1. Field of the Invention

This invention relates to the field of laboratory dryers such as those used to dry tissue samples and the like which may contain infectious pathogens, and in particular to a laboratory dryer with powered airflow means and a hydrophilic filter material disposed on an exhaust outlet thereof.

2. Prior Art

Laboratory dryers for tissue samples and the like are known with powered airflow means. The Quick-Dry laboratory dryer marketed by Micro Diagnostics Corporation of Bethlehem, Pa. is an example. In order to improve the rate of drying of the samples as compared to simply leaving the samples exposed to the air, the device comprises at least one fan for establishing a powered flow of air over the samples and at least one heater disposed in the flow path. These elements are mounted in a housing where the samples can be placed in a semi-enclosed environment, protected from airborne dust. However, the exhaust air, i.e., the air that has already passed over the samples, moves directly out of the housing into the room in which the dryer is located.

Any water droplets, particles and the like which are extracted from the samples by the powered airflow become airborne. These droplets and/or particles are emitted by the dryer and can be ingested by laboratory personnel during respiration or by contact with surfaces on which the droplets or particles may settle. The separation of droplets and particles from the samples is driven substantially by the powering of the airflow. However, a powered airflow is desirable in order to speed drying. Therefore, there is an inherent danger to laboratory personnel in accelerated drying of samples which may be infected with bacteria or viruses using the ambient air of the room wherein the dryer is located.

Laboratory dryers may be used, for example, to dry samples on microscope slides, in petri dishes or on trays, or materials which are otherwise supported so as to be subject to air passing through the dryer. The specific material dried can be cultures prepared from tissue samples or actual pieces of biological tissue from a subject to be tested. It may be desirable to dry some of these samples at a higher temperature and others at a lower temperature, as necessary to avoid inducing changes to the samples which may affect the results of further tests to be conducted on the samples.

According to the present invention, a laboratory dryer is provided with a filter at a point downstream in the air flow of the samples, for example at the exhaust outlet of the drying apparatus. The filter includes a body of hydrophilic filter material, preferably of synthetic fibers such as polyethylene, whereby water droplets which may be extracted from the samples in the drying process are absorbed and held by the filter material. The filter material is preferably framed such that it can be readily removed, for example for autoclaving.

Biological filter apparatus are disclosed, for example, in U.S. Pat. Nos. 3,703,961-Feuer; 3,482,703-Roberts et al; 3,910,778- Shawgholi; 4,670,223 -Dalachapella; and 4,604,110-Frazier. According to the preferred embodiment of the present invention, the filter material is simply a layer of hydrophilic fibrous filter material disposed across the outlet of the dryer. The noted references, however disclose a number of rather complicated alternatives for filter elements which are believed effective for blocking the passage of biologically dangerous materials such as bacteria and viruses. The teachings of these patents are nevertheless incorporated herein, particularly as to filters useful for high performance filter applications as appropriate for drying especially dangerous pathogen containing samples.

SUMMARY OF THE INVENTION

It is an object of the invention to resolve the competing needs to obtain fast drying of laboratory samples and to protect laboratory personnel from airborne particles and droplets which may contain contagious pathogens or toxic materials.

It is also an object of the invention to provide a safe and effective laboratory dryer at minimum cost and complexity as to manufacture, use and maintenance.

These and other objects are accomplished by a laboratory dryer especially for drying potentially infectious or toxic samples. The dryer has a housing with an air inlet and an air outlet, the housing defining an air flow path. The samples are received at a station within the housing between the inlet and the outlet along the air flow path, and subjected to a powered air flow via a fan. A hydrophilic filter element is disposed downstream along the air flow path from the samples and upstream of the outlet, such that air exhausted from the housing passes through the filter. The filter captures particulate matter and water droplets which would otherwise carry contagious or toxic material from the housing into the room. An electric heater is disposed in the housing adjacent the inlet and downstream of the fan. The housing can have an internal cross section of decreasing area proceeding towards the samples along the air flow path, whereby a velocity of the air over the samples is increased. The housing defines a plurality of compartments for receiving the samples along sections separated by at least one internal partition of the housing disposed parallel to the flowpath. The hydrophilic filter element is a fibrous batt of fibers disposed across the outlet, preferably synthetic fibers such as polyethylene fibers, mounted in a frame whereby the filter element can be readily removed.

BRIEF DESCRIPTION OF THE DRAWINGS

There are shown in the drawings the embodiments of the invention as presently preferred. It should be understood, however, that the invention is not limited to the precise arrangements shown, which are exemplary, and is capable of embodiment in other configurations in accordance with this disclosure and the appended claims. In the drawings.

DETAILED DESCRIPTION OF THE PREFERRED EMBODIMENTS

Figure 1:
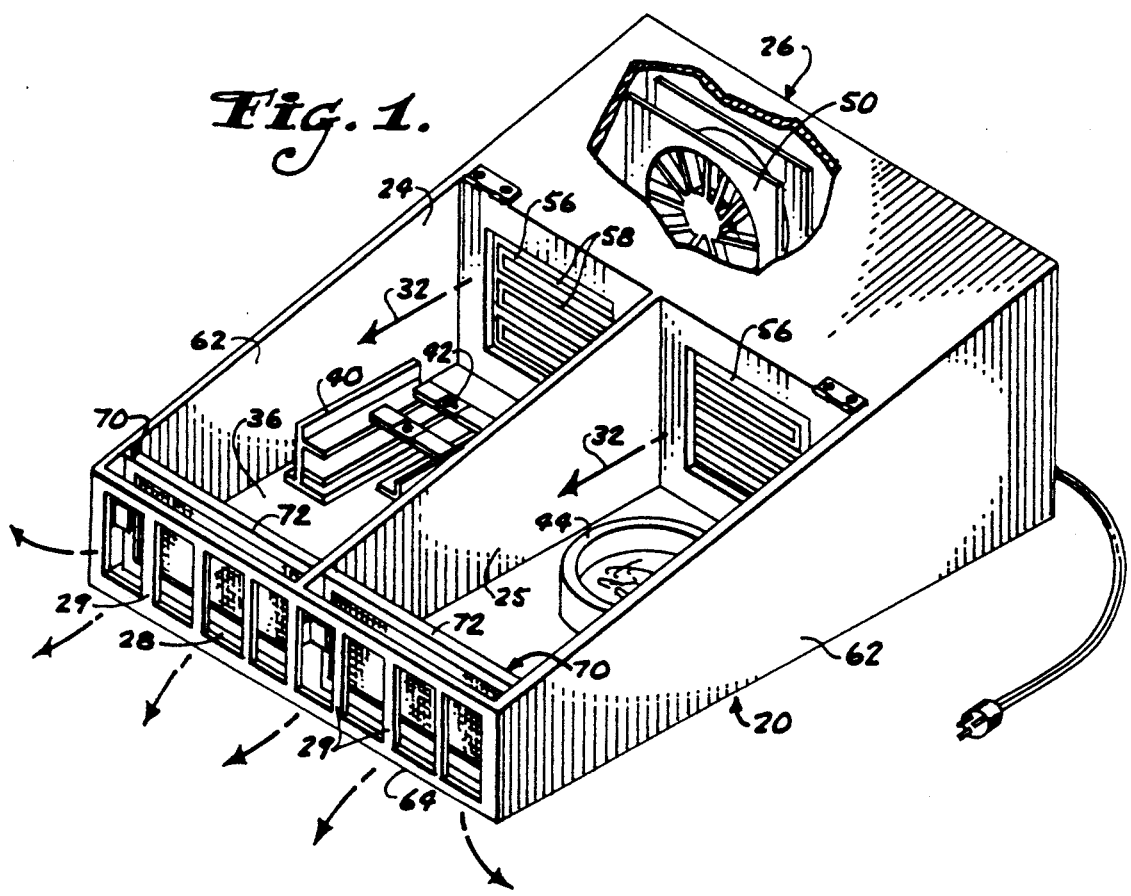
FIG. 1 is a perspective view of the laboratory dryer of the invention, shown partly cut away, and with the lid removed.

The laboratory dryer of the invention, as shown in the drawings, can be used in any setting in which samples are to be safely dried. In laboratories conducting diagnostic assessments, it is sometimes necessary to process tissue samples of patients which may be infected with contagious diseases. The tissue samples can be cultured, for example together with agents indicating immune responses to particular pathogens for which a test is being conducted. The tissue samples themselves may be treated with an agent producing a detectable change in attributes (e.g., color) of the samples in the event a test result is positive. Before further processing or before viewing the processed samples via a microscope, it is sometimes desirable that the samples be dried. During drying, the samples can release airborne water droplets and/or small particles into the air flow, which then carries the contagious material out of the housing and into the ambient air of the room. Laboratory personnel can become infected by ingesting the contagious material, for example by respiration or by contact with surfaces on which the particles or droplets may settle. The present invention facilitates drying while isolating the contagious or toxic materials which may be emitted from the sample as a result of the drying process, and carried on water droplets or particulate matter. These particles and droplets are captured by a hydrophilic filter element through which the dryer exhaust is passed.

In order to speed drying, the laboratory drier 20 of the invention includes a housing 24 with at least one area 36 where the samples to be dried can be placed. The housing 24 can be opened and closed for access to the sample area and to confine the samples during the drying process. The housing 24 defines an air inlet 26, disposed at the rear of the device as shown in FIG. 1, and an air outlet 28, disposed at the front, each communicating with the ambient air of the room. When the housing 24 is closed by its lid (not shown in FIG. 1), the housing defines an air flow path from the inlet 26 to the outlet 28, which air flow path encompasses the sample station at area 36. In the embodiment shown, there are two sample areas 36, separated from one another by partition 25, and two complete drying apparatus associated therewith. These two apparatus can be operated independently or simultaneously.

The air flow path exits the housing after passing over the samples. To minimize the extent to which the exiting air can emit toxic or contagion carrying particulate matter and water droplets into the room in which the drier is located, a hydrophilic filter element 70 is disposed downstream along the air flow path from the samples and upstream of the outlet into the room. The filter element 70 captures particulate matter and water droplets extracted from the samples by the air flow, which would otherwise carry them from the housing into the room.

According to the preferred embodiment, an electric heater 56 is included upstream of the samples, for lowering the relative humidity of the air (i.e., by raising its temperature) to improve drying. The housing 24 also preferably has an internal cross section that concentrates the air flow on the samples, for example by decreasing in cross sectional area proceeding towards the samples along the air flow path, whereby a velocity of the air over the samples is increased. The housing can also widen in area downstream of the samples, to decrease the linear velocity of the air flow when passing through the filter.

The preferred hydrophilic filter element is a simple fibrous batt of fibers disposed across the outlet, preferably synthetic fibers such as polyethylene fibers which absorb liquids and block passage of particles. The filter element is mounted in a frame and placed under the lid such that the filter element can be readily removed for replacement and/or cleaning. When the filter element is mounted and the lid is closed, the filter element substantially seals across the internal cross section of the housing at a point downstream of the samples.

Figure 2:
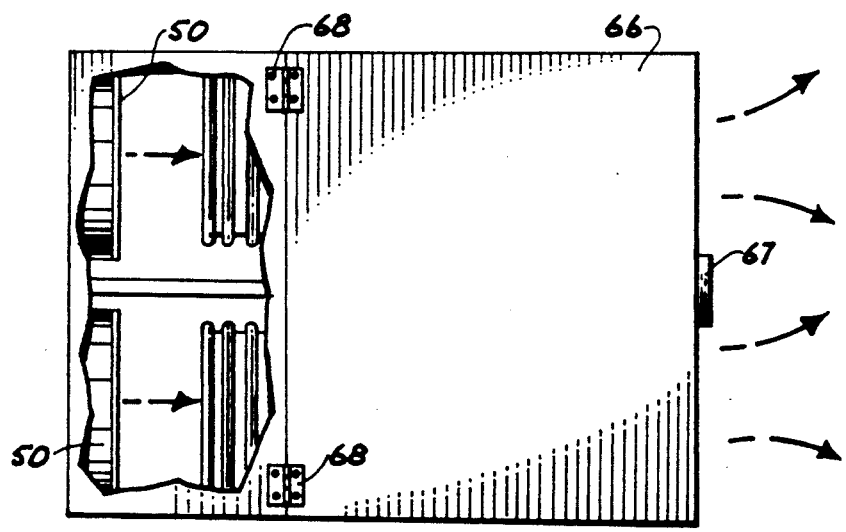
FIG. 2 is a plan view of the dryer as shown in FIG. 1 with the lid in place and closed, and with the housing partly cut away.
Figure 3:
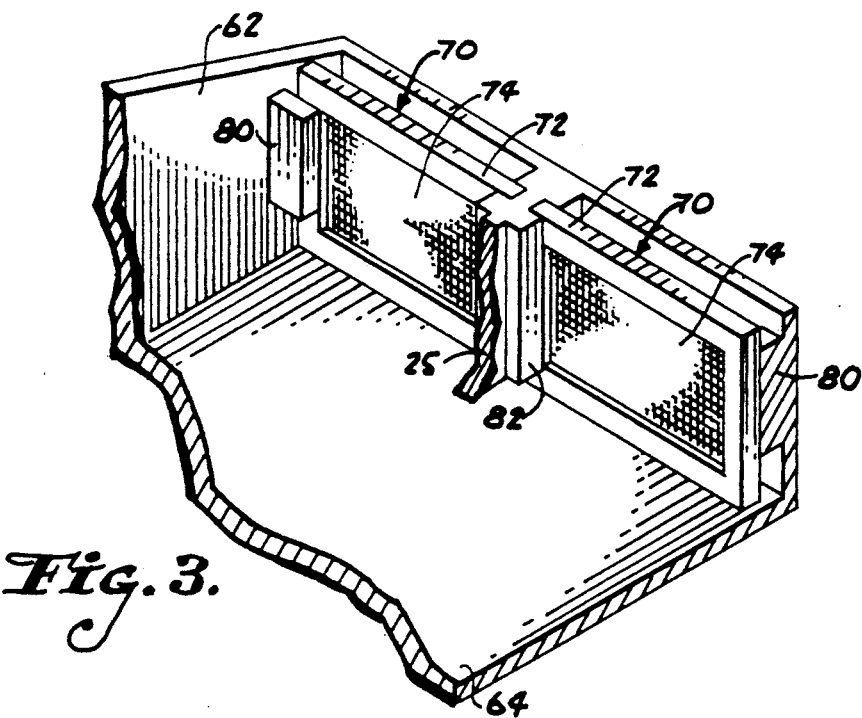
FIG. 3 is a partial perspective view of the air outlet area of the housing, partly cut away.

With reference to FIGS. 1-3, a laboratory dryer 20 comprises a housing 24 having an air inlet 26 and an air outlet 28, the housing 24 having internal surfaces defining an air flow path from the inlet 26 to the outlet 28, as indicated by arrows 32. The air inlet at the rear of the housing has not been shown in detail, and may be formed by a simple opening. Alternatively, a series of perforations or other fenestrations may be provided in the rear wall of the housing 24, to allow airflow. An electrically powered airflow means is included for drawing air into the housing through the inlet 26, and forcing the air through the outlet 28. The outlet 28 likewise is preferably a simple opening or series of openings in the front wall of the housing. In the preferred embodiment as shown in FIG. 1, outlet 28 is elongated to substantially cover the entire front wall of the housing, and a series of bars 29 bridge across the opening to protect the internal area, and specifically to prevent contact with the filter element 70, disposed behind the bars 29.

In the area or areas 36 where the samples are to be located, means are provided for receiving samples to be dried. The samples can be placed on the inner surface of the bottom 64 of the housing, or more elaborate means can be provided as shown, for supporting the samples themselves, or trays or the like for holding the samples. In the embodiment shown, samples in the form of microscope slides 42 and petri dish containers 44 are disposed in the sample area 36 between the inlet 26 and the outlet 28 along the air flow path 32. As shown, the slides are received on a rack 40 placed in the sample area 36, and petri dish 44 is simply placed on the inner surface of the bottom wall 64 of the housing. Various other support means may be included or may be replaceably used, for example supports for swabs, vials, test strips, etc.

FIG. 2 shows the apparatus with the lid 66 in place. Lid 66 can be mounted to the top wall of the housing 24 by means of hinges 68 as shown. Alternatively, the lid 66 can be removably fittable on the opening over the sample area. Preferably, lid 66 covers both the sample area(s) 36 and the area of filter element 70, whereby access to both is obtained by removing the lid or by hinging it upwardly. In the preferred unit, the rear portion of the housing holding the electrical air flow powering means remains sealed.

It may be possible to arrange a powered air flow means driven only by thermal currents produced by a heater. It is also possible to forego the heater and to power the air flow using a fan only. According to the preferred embodiment, however, the air flow is electrically powered by means of fan 50 and a heater 56. The fan 50 can be upstream of the coils 58 of electric heater 56 (thereby remaining cooler). The fan 50 can be a tube axial fan, for example a MUFFIN fan or the like, and is disposed within the housing 24, immediately adjacent the inlet 26. A supplemental dust filter (not shown) can be placed upstream of the fan 50, for example on a mounting on the external surface of the housing 24, which helps to avoid drawing dust into the drier and/or possible contamination of the samples with airborne particles from the room.

FIGS. 1 and 3 illustrate the mounting of the filter element adjacent the outlet 28 of the drier 20. Hydrophilic filter element 70 is disposed downstream along the air flow path 32 from the samples 40, 44 and upstream of the outlet 28. The lid 66 fits down over the top edge of the filter element 70, and accordingly, substantially all the air moving over the samples must pass through the filter element 70, where droplets are absorbed and particles are blocked. The filter element 70 includes a fibrous batt of fibers forming a layer of filter material 74 disposed across the outlet 28. The fibrous batt of fibers is preferably mounted in a frame 72. The frame can fit removably in a receptacle for the filter element adjacent the outlet 28. The receptacle can include flange blocks 80, 82, which together define a slot into which the frame 72 of the filter element 70 can slide, being thereby held in place at the outlet 28. Other alternatives are also possible, for example spring clips, flanges disposed on the bottom of housing bottom wall 64, or slots formed in the housing walls. In the embodiment shown, the filter element frame 72 is received in a slot-like receptacle formed between the laterally outer blocks 80 and the central blocks 82.

The filter can be finer for more demanding applications requiring blockage of smaller particles and droplets, or more coarse, where the filter element need block only relatively larger particles and droplets. The filter can also include means defining a tortuous path through the filter (to better obtain contact between droplets and the fibers), electrostatic means for capturing particles, charcoal sections, and other features as disclosed for example in the references mentioned in the prior art section herein above. Preferably, however, the filter material is simply a sheet of polyester fibers carried in the frame 72. The thickness of the fibrous bat can also be varied according to the application. The preferred fibers are synthetic resin fibers, for example polyester fibers. A range of fiber sizes and thicknesses in a bonded fiber polyester material is available from the Dupont Corporation, Wilmington, Del., under the trademark REEMAY.

Figure 4:
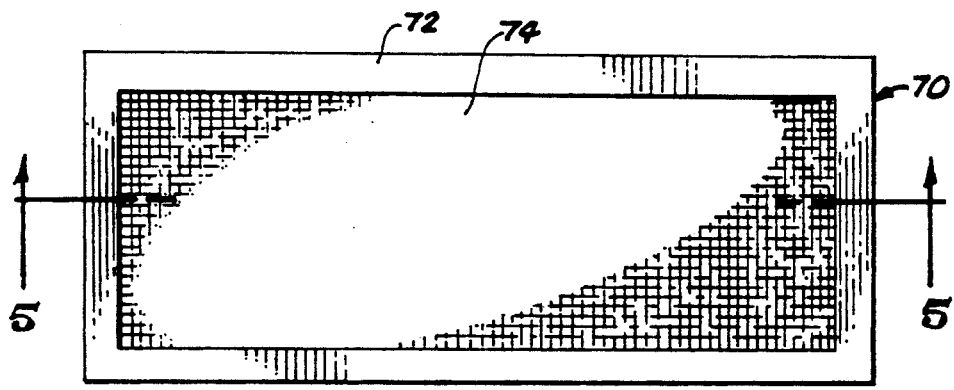
FIG. 4 is an elevation view of the filter element according to the invention.
Figure 5:
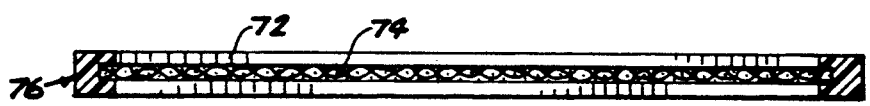
FIG. 5 is a section view taken along lines 5—5 in FIG. 4.
Figure 6:
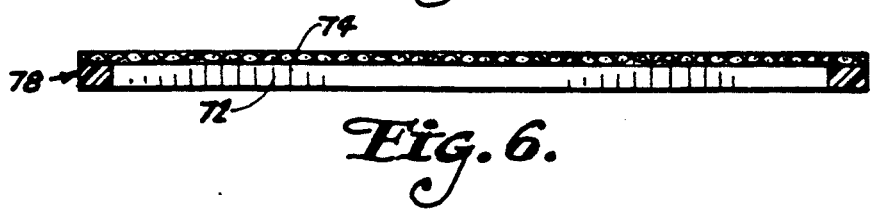
FIG. 6 is a section view of an alternative embodiment, corresponding to the view in FIG. 4.

A preferred filter element according to the invention is shown in FIGS. 4–6. Filter element 70 has a frame 72 bonded to peripheral edges of the fibrous sheet 74 of the filter element. According to FIG. 5, a filter element 76 has a fibrous hydrophilic sheet 74 bonded to frame 72 such that the frame protrudes from the sheet 72 on both sides. This structure can be formed, for example, by bonding together two frame halves over the filter sheet 74 by means of adhesives or by chemical or heat welding. According to FIG. 6, filter element 78 has a sheet 74 of hydrophilic filter material bonded to frame 72 on one side, for example by adhesive or by heat bonding.

The housing 24 according to the preferred embodiment defines an internal cross section of decreasing area proceeding towards the sample area 36 along the air flow path 32. In this manner, the linear velocity of the air is increased at the samples 40, 44, compared to the linear velocity of the air upstream, i.e., at the fan 50. It is also possible to vary the cross sectional area downstream of the samples, for example increasing the cross sectional area at the filter element 70.

The housing 24 has separable top 66 and bottom sections 62, 64, which can be fully separable or hingeable as shown. In any event, the sections include panels which are relatively movable for access to at least one of the samples and the filter element. If desired, a separate cover or movable panel can be provided for access to the filter element, for access to the overall sample area, or for access to individual ones of the sample areas. The housing has one or more internal partitions 25 (shown in FIGS. 1 and 3) disposed parallel to the flow path, separating the sample chambers into a plurality of compartments which are isolated from one another. These compartments can each be provided with an individual fan 50, heater 56 and filter 70. The individual fans and heaters can be operated independently, such that appropriate conditions in the compartments (i.e., particular heating and air flow rates) can be set to a specific level as appropriate for samples being processed. The heaters 56 and/or fans 50 can be provided with on-off controls or continuously variable or stepwise variable controls for fixing the respective rates.

The invention having been disclosed, a number of additional variations and alternatives within the scope of the invention will now become apparent to persons skilled in the art. Reference should be made to the appended claims rather than the foregoing specification in assessing the scope of the invention in which exclusive rights are claimed.

We claim:

1. A laboratory dryer, comprising:
 a housing defining an enclosure for placement in a room, the housing having an air inlet and an air outlet communicating with ambient air in the room, the housing defining an air flow path from the inlet to the outlet;
 means for receiving samples to be dried, disposed between the inlet and the outlet along the air flow path;
 an electrically powered airflow means operable to draw air into the inlet and force the air through the outlet;
 a hydrophilic filter element disposed downstream along the air flow path from the sample receiving means and upstream of the outlet, the filter element comprising a hydrophilic fibrous filter material, the filter element being operable to absorb droplets and capture particles from air moving toward the outlet, whereby moisture and particles released from the samples are confined to the housing; and,
 wherein the housing defines an internal cross section of decreasing area proceeding over the sample receiving means along the air flow path, whereby a velocity of the air over the samples is increased.

2. The laboratory dryer according to claim 1, wherein the electrically powered airflow means includes at least one of a fan and a heater, disposed in the housing adjacent the inlet.

3. The laboratory dryer according to claim 1, wherein the electrically powered airflow means comprises at least one fan for forcing air along the air flow path and at least one electric heater placed upstream of the sample receiving means along the air flow path.

4. The laboratory dryer according to claim 1, wherein the hydrophilic filter element includes a fibrous batt of fibers disposed across the outlet.

5. The laboratory dryer according to claim 4, wherein the fibrous batt of fibers is mounted in a frame, and further comprising a receptacle for the filter element adjacent the outlet.

6. The laboratory dryer according to claim 4, wherein the fibers are synthetic resin fibers.

7. The laboratory dryer according to claim 6, wherein the fibers are polyester fibers.

8. The laboratory dryer according to claim 6, further comprising a frame bonded to peripheral edges of the filter element.

9. The laboratory dryer according to claim 1, wherein the housing has at least one panel which is movable relative to the housing for access to at least one of the samples and the filter element.

10. The laboratory dryer according to claim 9, wherein the housing has at least one movable top section which can be separated from a bottom section for access to said at least one of the samples and the filter element.

11. The laboratory dryer according to claim 1, wherein the housing defines a plurality of compartments for receiving the samples along sections separated by internal partitions of the housing disposed parallel to the flowpath.

12. A laboratory dryer, comprising:
a housing defining an enclosure for placement in a room, the housing having an air inlet and an air outlet communicating with ambient air in the room, the housing defining an air flow path having a section of decreasing cross section proceeding along the air flow path from the inlet to the outlet;
means for receiving samples to be dried, disposed between the inlet and the outlet in the section of decreasing cross section along the air flow path;
an electrically powered airflow means operable to draw air into the inlet and force the air through the outlet;
a heater disposed between the inlet and the means for receiving samples; and,
a hydrophilic filter element consisting essentially of a panel of synthetic resin fibers defining a hydrophilic filter material, the filter element being disposed downstream along the air flow path from the sample receiving means and upstream of the outlet, the filter element being operable to absorb droplets and capture particles from air moving toward the outlet, whereby moisture and particles released from the samples are confined to the housing.

13. The laboratory dryer according to claim 12, wherein the filter element comprises a fibrous batt of fibers mounted in a frame, and further comprising a receptacle for the filter element adjacent the outlet.

14. The laboratory dryer according to claim 12, wherein the fibers are polyester fibers.

15. The laboratory dryer according to claim 14, further comprising a frame bonded to peripheral edges of the filter element.

* * * * *